United States Patent [19]

Heumann et al.

[11] Patent Number: 4,796,613
[45] Date of Patent: Jan. 10, 1989

[54] LITHOTRIPSY WORK STATION

[75] Inventors: Reiner Heumann, Spardorf; Erich Noske, Weiher; Manfred Rattner, Buckenhof, all of Fed. Rep. of Germany

[73] Assignee: Siemens Aktiengesellschaft, Berlin and Munich, Fed. Rep. of Germany

[21] Appl. No.: 912,043

[22] Filed: Sep. 26, 1986

[30] Foreign Application Priority Data

Oct. 9, 1985 [DE] Fed. Rep. of Germany ....... 3536091
Dec. 6, 1985 [DE] Fed. Rep. of Germany ....... 3543265

[51] Int. Cl.$^4$ ............................................. A61B 17/22
[52] U.S. Cl. .................................. 128/24 A; 128/328; 378/196
[58] Field of Search ...................... 128/328, 24 A, 1 R; 269/322, 323, 324, 325, 326, 327, 328; 378/196, 197, 41, 92

[56] References Cited

U.S. PATENT DOCUMENTS

| | | | |
|---|---|---|---|
| 2,508,449 | 5/1950 | Davis et al. | 378/196 |
| 3,302,022 | 1/1967 | Brenner et al. | 378/196 |
| 3,549,885 | 12/1970 | Anderson | 378/197 |
| 3,652,851 | 3/1972 | Zaalberg | 269/322 |
| 4,131,802 | 12/1978 | Braden et al. | 269/322 |
| 4,287,422 | 9/1981 | Kuphal et al. | 264/327 |
| 4,426,725 | 1/1984 | Grady | 378/196 |
| 4,506,872 | 3/1985 | Westerberg et al. | 269/322 |
| 4,539,989 | 9/1985 | Forssmann et al. | 128/328 |
| 4,610,249 | 9/1986 | Makofski et al. | 128/328 |
| 4,620,545 | 11/1986 | Shene et al. | 128/24 A |
| 4,669,483 | 6/1987 | Hepp et al. | 128/328 |
| 4,705,026 | 11/1987 | Chaussy et al. | 128/328 |

FOREIGN PATENT DOCUMENTS

| | | | |
|---|---|---|---|
| 0133946 | 3/1985 | European Pat. Off. | |
| 205878 | 12/1986 | European Pat. Off. | 128/328 |
| 2418631 | 10/1975 | Fed. Rep. of Germany | 128/24 A |
| 3220751 | 12/1983 | Fed. Rep. of Germany | |
| 3517934 | 11/1986 | Fed. Rep. of Germany | 128/328 |
| 2038150 | 7/1980 | United Kingdom | |
| 8503631 | 8/1985 | World Int. Prop. O. | |

OTHER PUBLICATIONS

Chassy et al, "Extracorporeal Shock Wave Lithotripsy", 1982.

Primary Examiner—Ruth S. Smith
Attorney, Agent, or Firm—Hill, Van Santen, Steadman & Simpson

[57] ABSTRACT

A lithotripsy work station has a table for supporting a patient which is adjustable in three spatial directions, with at least one shock wave generator disposed below the table. The shock wave generator is adjustably mounted so that movement of its focus to an isocenter is possible. For locating renal calculi, an x-ray examination apparatus is provided which transilluminates the patient at various angles. A plane defined by two central rays of the x-ray apparatus proceeds through the longitudinal axis of the patient supporting table, such that one radiator of the x-ray system emits radiation in an a.p.-direction and a second radiator of the x-ray apparatus emits radiation in the caudal-cranial direction. The x-ray radiators can be moved out of the work area, as needed. The work station can be used for shock wave treatments, for urological treatments and for x-ray examinations.

9 Claims, 8 Drawing Sheets

LITHOTRIPSY WORK STATION

BACKGROUND OF THE INVENTION

The present invention relates to a lithotripsy work station which may be employed, for example, for disintegrating kidney stones and other types of calculi.

In many conventional stations for externally applying shock waves to a patient to disintegrate calculi, the patient must be placed in a tub filled with water which acts as a medium via which shock waves from a shock wave generator are transmitted to the calculi for disintegration thereof.

It is an object of the present invention to provide a universal lithotripsy work station which permits the following operations to be undertaken:

(1) Shock wave treatment, particularly disintegration of renal and ureteral calculi.

(2) Urological treatments including percutaneous nephrostomy.

(3) X-ray examinations.

The above objects are achieved in accordance with the principles of the present invention in a lithotripsy work station which includes a patient supporting table which is adjustable in three directions, with at least one shock wave generator for renal calculi disintegration being arranged beneath the table. The shock wave generator can be coupled to the patient's skin via a membrane. The shock wave generator is adjustably mounted so that movement of the focus thereof to an isocenter is possible.

For locating renal calculi, an x-ray examination apparatus is provided which includes an x-ray unit for transilluminating at various angles. The x-ray apparatus has two x-radiators, each of which emits a central ray. The plane defined by the two central rays passes through the longitudinal axis of the patient supporting table, with the radiators disposed such that one radiator emits radiation in an anterior-posterior (a.p.)-direction and the second radiator emits radiation in the caudal-cranial (c.c.) direction. The patient supporting table includes means for accomodating attachment of auxiliary urological equipment and for attachment of an x-ray exposure means.

In one embodiment of the invention, the radiators of the x-ray apparatus are both mounted in a common housing which is adjustable in a vertical plane. In this embodiment, it is possible to displace the radiators upwardly in the examination room when they are not required for locating calculi. The radiators can be displaced upwardly to such a degree that they do not impede the physician in any activities which he or she may undertake, particularly for percutaneous operations. The housing may include a universal connector for optional connection the ceiling or wall of the examination room, or to a vertical post.

DESCRIPTION OF THE PREFERRED EMBODIMENTS

Figure 1:
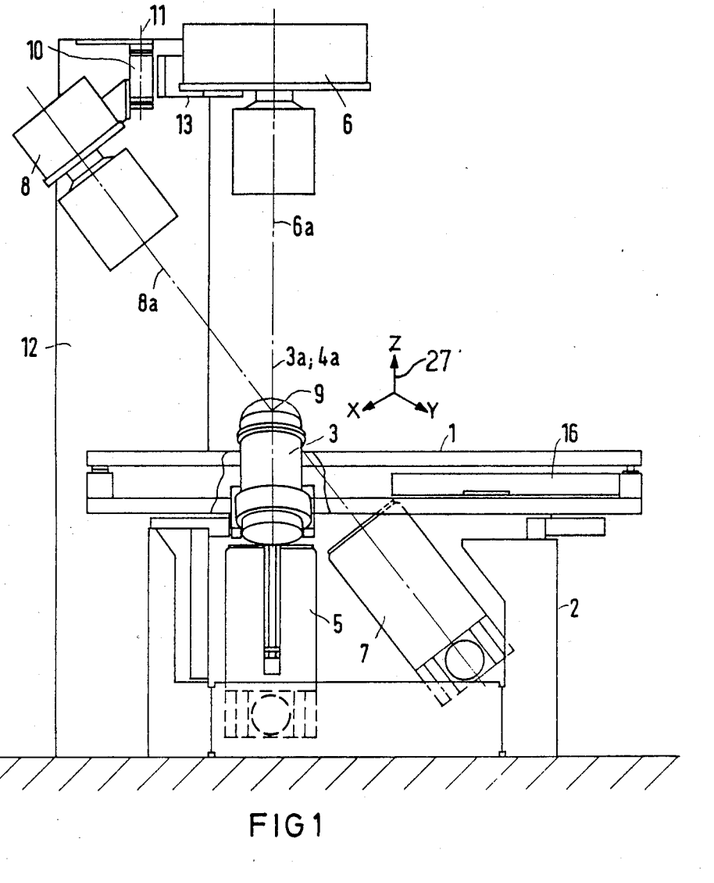
FIG. 1 is a side elevational view of a lithotripsy work station constructed in accordance with the principles of the present invention.
Figure 2:
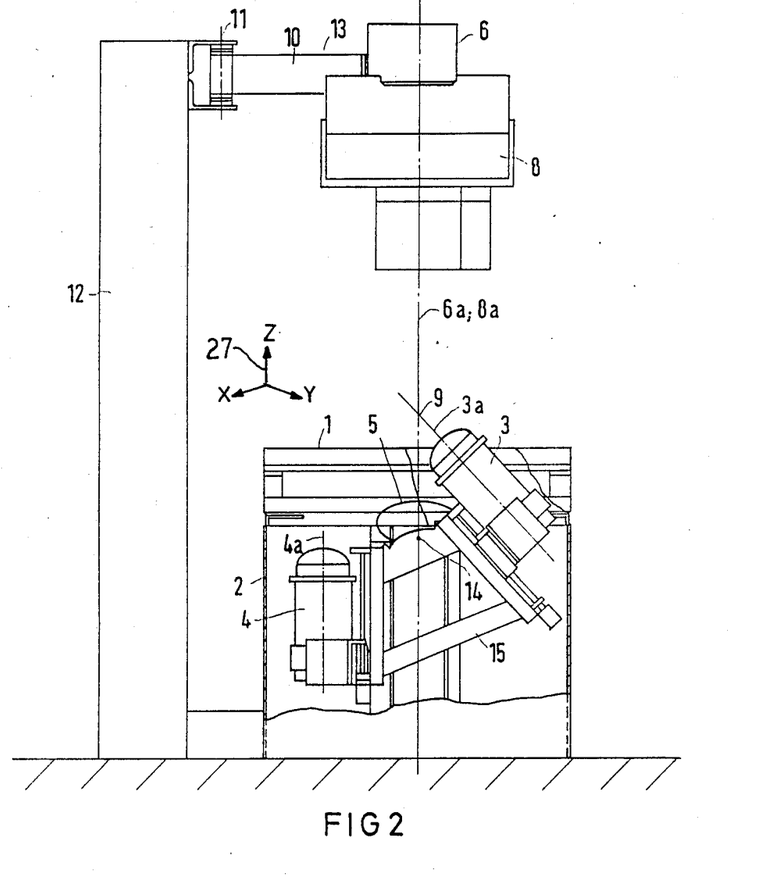
FIG. 2 is an end elevational view of the lithotripsy work station shown in FIG. 1.

A lithotripsy work station constructed in accordance with the principles of the present invention in a first embodiment is shown in FIGS. 1 and 2. The station includes a patient supporting table 1 adjustable along three perpendicular axes, schematically indicated by the coordinate system 27, in a manner known to those skilled in the art as shown, for example, in U.S. Pat. No generators 3 and 4 are arranged. The shock wave generators 3 and 4 can best be seen in FIG. 2; and in FIG. 1 the shock wave generator 4 is covered by an x-ray image intensifier 5. Together with an x-ray radiator 6, the x-ray image intensifier 5 forms a first x-ray system, the x-ray radiator 6 emitting radiation perpendicular to the patient supporting table 1 in an a.p.-direction.

A second x-ray system is formed by another x-ray image intensifier 7 and another x-ray radiator 8. The x-ray radiator 8 emits radiation in the caudal-cranial direction.

As a result of the different directions of the central rays 6a and 8a of the respective x-ray systems, renal calculi to be disintegrated can be located. The central rays 6a and 8a intersect at an isocenter 9 (i.e., a fixed point in space), to which the renal calculus to be disintegrated is displaced by appropriate movement of the patient supporting table 1, with a patient thereon.

The plane defined by the two central rays 6a and 8a proceeds through the longitudinal axis of the patient supporting table 1, so that the lateral space requirement for the x-ray units is small.

The x-ray radiator 8 is secured to an arm 10 which is mounted to a post 12 so as to be pivotable around a vertical axis 11. It is thus possible to pivot the x-ray radiator 8 out of the work area, as needed.

The x-ray radiator 6 is also connected to the post 12, by means of an arm 13 which permits the x-ray radiator 6 to be displaced at right angles relative to the longitudinal axis of the patient supporting table 1. The x-ray radiator 6 thus can also be moved out of the work area, as needed.

The shock wave generators 3 and 4 are mounted on a common support 15, best seen in FIG. 2, which is pivotable around an axis 14 extending parallel to the longitudinal axis of the table. The shock wave generators 3 and 4 are mounted on the support 15 such that their respective axes 3a and 4a intersect at an angle. Each shock wave generator 3 and 4 is adjustable in the direction of its respective axis 3a and 4a.

For shock-wave treatment of a patient, the patient is seated on the patient supporting table 1 and the calculus to be disintegrated is moved into the isocenter 9 under x-ray supervision. Subsequently the axis 3a or 4a of one of the shock wave generators 3 or 4 is directed to the isocenter, and that shock wave generator is moved toward the patient through an opening in the patient supporting table 1 until a membrane of the shock wave generator presses against the skin of the patient. The shock wave treatment can subsequently ensue.

Figure 3:
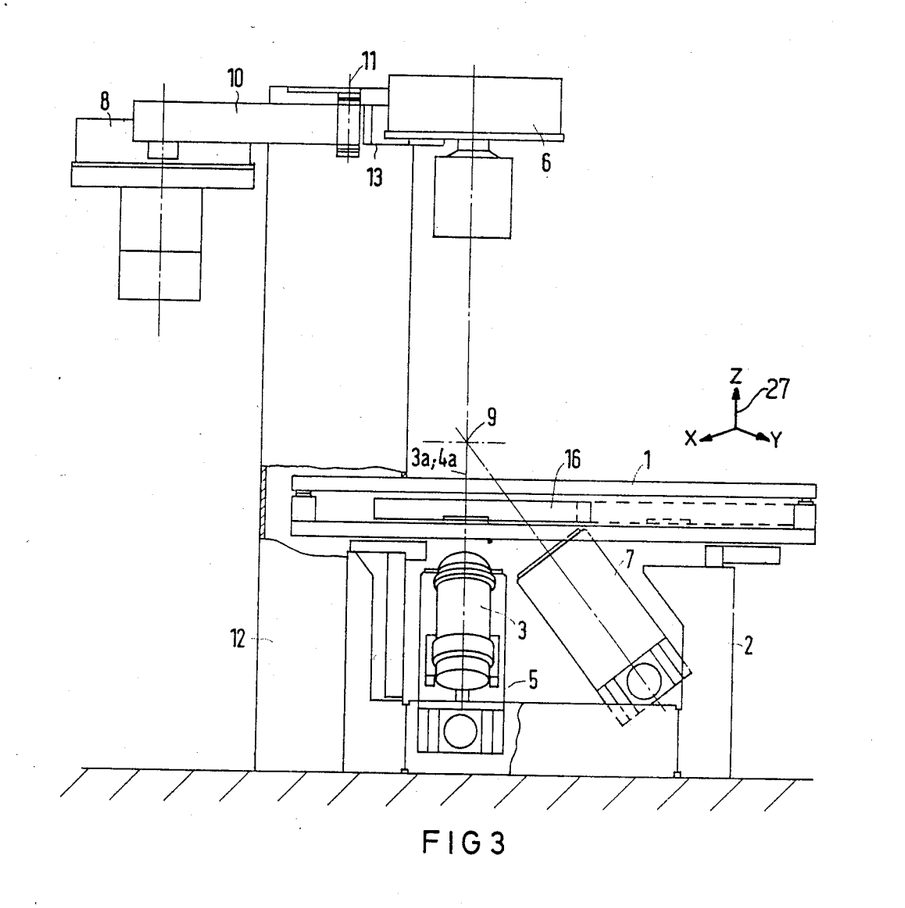
FIG. 3 is a side elevational view of a lithotripsy work station constructed in accordance with the principles of the present invention with a modified positioning of the x-ray radiator.
Figure 4:
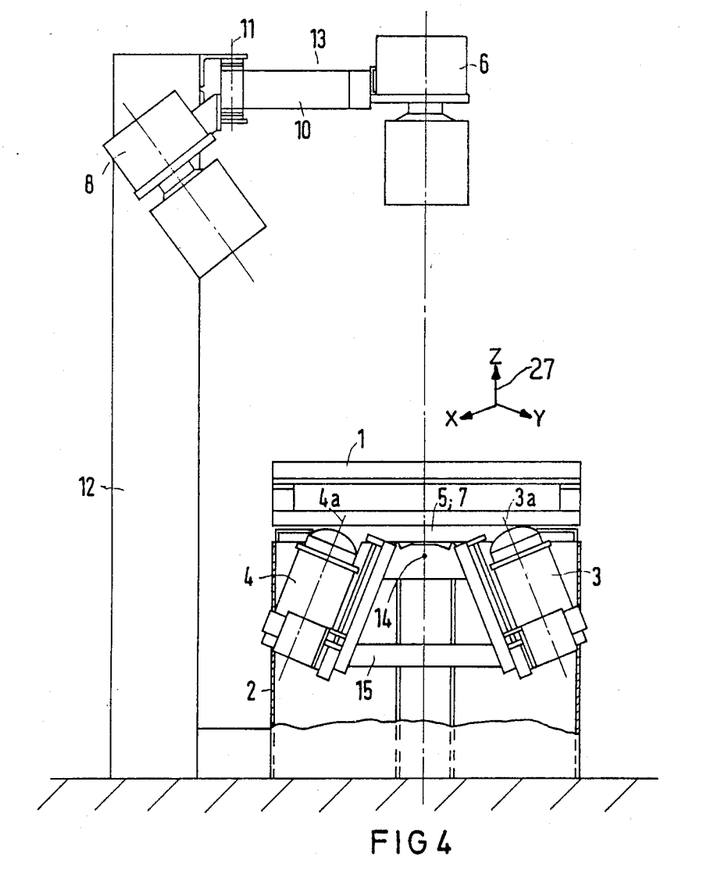
FIG. 4 is an end view of the lithotripsy work station shown in FIG. 3.

For the introduction of an x-ray film cassette, the support 15 can be used to move the shock wave generators 3 and 4 to the position shown in FIG. 4, permitting an x-ray film cassette 16 to be adjusted to an exposure position shown in FIG. 3. In FIG. 1, the x-ray cassette 16 is shown in a preparatory or standby position, in which the space under the calculus to be disintegrated is maintained free for application of one of the shock generators 3 or 4. The shock wave generators 3 and 4 are respectively allocated to the two kidneys.

The patient supporting table 1 has means for attaching urological auxiliary equipment, for example containers, so that standard urological routines can be undertaken. The lithotripsy work station disclosed herein can be used as a standard x-ray work station for transillumination and exposure.

It is also possible to omit the pivoting capability of the support 15 if the support 15 is arranged such that the longitudinal axes of the two shock wave generators 3 and 4 intersect at the isocenter 9.

Instead of two x-ray systems for transilluminating the patient at different angles, only one such system, having one or two image intensifiers, may be used if mounted in an appropriately adjustable manner. It is also possible to provide a single stationary x-ray system including an image intensifier if a stereo x-ray tube is employed.

Coupling of the patient to the shock wave generators 3 and 4 via a water-filled tub is not required as a result of the use of shock wave generators 3 and 4 designed as individual units to be applied directly to the surface of the patient.

In the embodiment shown in FIGS. 5 and 6, components already described in connection with FIGS. 1 through 4 are identified with the same reference symbols. In this embodiment, the patient supporting table 1a is somewhat shorter than the patient supporting table 1 shown in the previous embodiments. The shock wave generators 3 and 4 are adjustable only along the directions of the two axes 3a and 4a, which intersect at the isocenter 9. Instead, the base 2a occupies a slightly greater width than the previously-described base 2.

Figure 5:
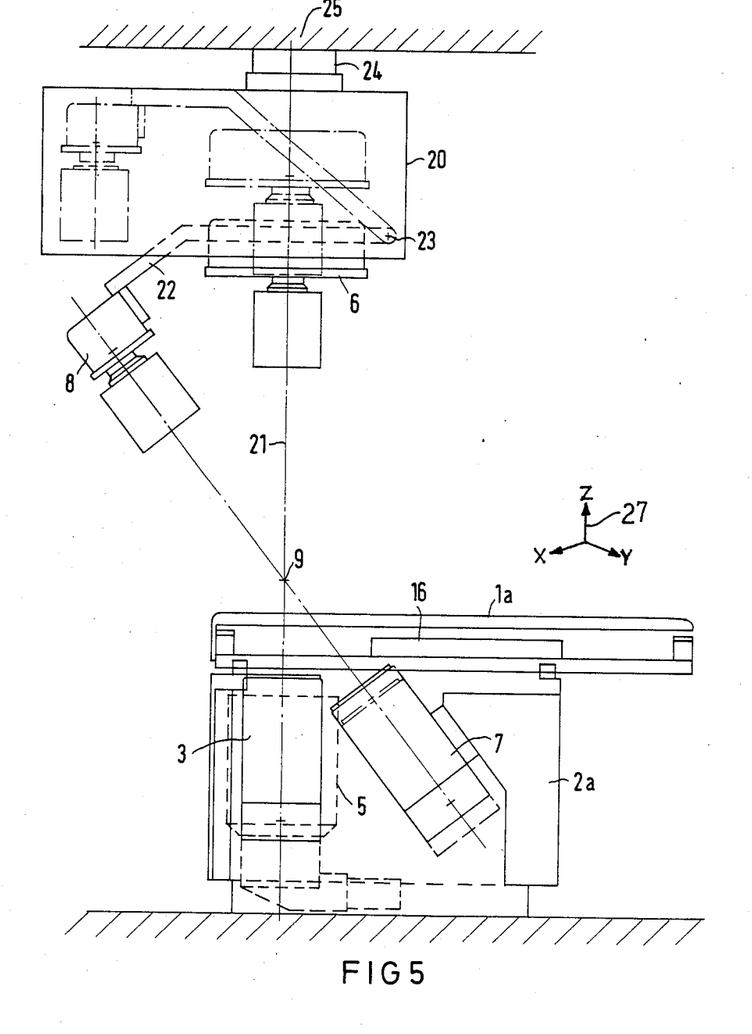
FIG. 5 is a side view of another embodiment of a lithotripsy work station constructed in accordance with the principles of the present invention.
Figure 6:
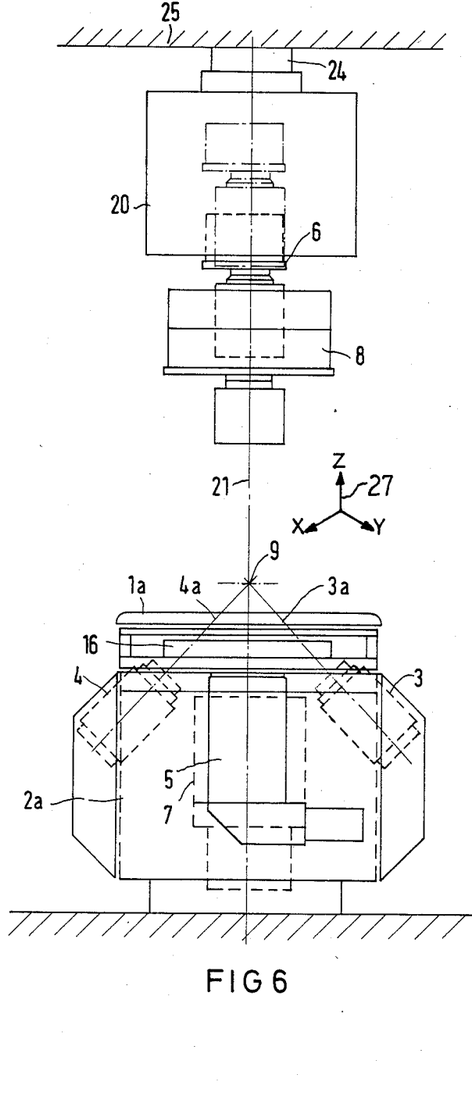
FIG. 6 is an end view of the lithotripsy work station shown in FIG. 5.

Also in the embodiment of FIGS. 5 and 6, the x-ray radiators 6 and 8 are mounted in a common housing 20, which is adjustable in a vertical plane. For this purpose, the x-ray radiator 6 is adjustable in the direction of the central ray 21, whereas the x-ray radiator 8 is secured to an arm 22 which is pivotable about an axis 23. The respective positions of the x-ray radiators 6 and 8 within the housing 20, when they are not being used, is indicated with broken lines in FIG. 5. The housing 20 is provided with a universal connector 24 which may, for example, be secured to the ceiling 25 of the examination room.

For locating calculi, the radiators 6 and 8 assume the positions shown with solid lines in FIGS. 5 and 6. When they are no longer required, the radiators are moved into the housing 20 and do not interfere with further treatment, for example during percutaneous operations (percutaneous nephrostomy), so that free access to the patient is insured.

Figure 7:
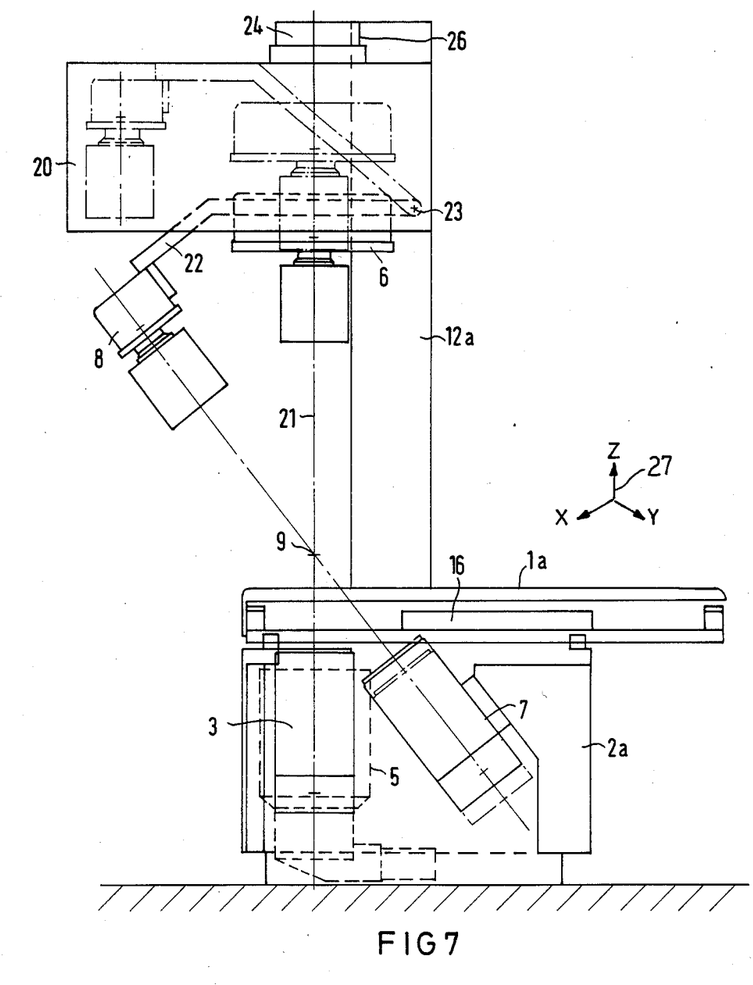
FIG. 7 is a side view of a lithotripsy work station constructed in accordance with the principles of the present invention with another modification of the x-radiator mounting.
Figure 8:
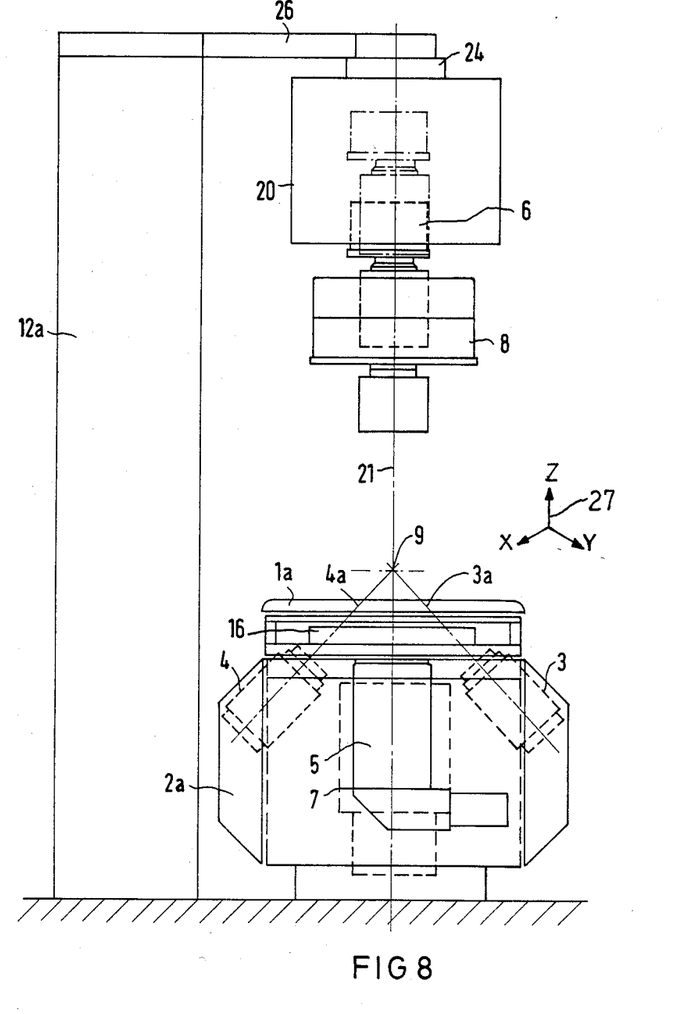
FIG. 8 is an end view of the lithotripsy work station shown in FIG. 7.

Another modification for mounting the x-ray radiators is shown in FIGS. 7 and 8. In this embodiment, the universal connector 24 is secured to an arm 26 which is connected to a column or post 12a, which is inturn supported on the floor of the examination room. Alternatively, the arm 26 may be secured to a vertical wall of the examination room.

Although modifications and changes may be suggested by those skilled in the art it is the intention of the inventors to embody within the patent warranted hereon all changes and modifications as reasonably and properly come within the scope of heir contribution to the art.

We claim as our invention:

1. A lithotripsy work station comprising:
   a patient support table having a longitudinal axis for selectively positioning a patient thereon with respect to a fixed point in space;
   at least one shock wave generator for disintegrating calculi disposed beneath said patient support table, said shock wave generator having a membrane for coupling said shock wave generator to the skin of said patient, and said patient support table having an opening therein through which said shock wave generator can at least partially extend;
   means for mounting said shock wave generator for permitting adjustment of the focus of said shock wave generator to said fixed point in space; and
   an x-ray examination means for transilluminating said patient at selected angles for locating calculi, said x-ray examination means including two x-ray radiators disposed above said patient support table and each having a central ray, a central ray of one of said radiators being emitted in a direction perpendicular to said patient support table and the central ray of the other radiator being emitted in an oblique direction with respect to said patient support table, with both of said central rays proceeding in a common plane which includes said longitudinal axis of said patient support table and intersecting in said fixed point in space 2. A lithotripsy work station as claimed in claim 1 further comprising:
   x-ray exposure means for generating an x-ray image from each of said x-ray radiators; and
   means for accomodating attachment of said x-ray exposure means beneath said patient support table.

3. A lithotripsy work station as claimed in claim 1 having two shock wave generators, and further comprising:
   a common support for said two shock wave generators;
   each shock wave generator having a central wave propagation axis and said shock wave generators being mounted on said support such that their respective propagation axes intersect at an angle;
   means for pivoting said common support about an axis parallel to said longitudinal axis of said patient support table to position one of said shock wave generators with its propagation axis proceeding through said fixed point in space; and
   means for adjusting the position of each shock wave generator relative to said common support along the direction of its propagation axis.

4. A lithotripsy work station as claimed in claim 1, wherein said x-ray examination means includes means for adjusting the radiator having a central ray emitted perpendicular to said patient support table at right angles relative to said patient support table.

5. A lithotripsy work station as claimed in claim 1, wherein said x-ray examination means includes means for moving the radiator having a central ray emitted in an oblique direction out of a work area above said patient support table 6. A lithotripsy work station as claimed in claim 1 further comprising a common housing for both of said x-ray radiators, and means in said housing for vertically adjusting the position of each of said radiators.

7. A lithotripsy work station as claimed in claim 6 wherein said housing includes means for supporting said housing on a horizontally disposed surface.

8. A lithotripsy work station as claimed in claim 7 wherein said horizontal surface is a horizontaly extending arm connected to a vertically disposed surface.

9. A lithotripsy work station as claimed in claim 8 for use in an examination room having a floor, wherein said vertically disposed surface is a post supported on the floor of said examination room.

* * * * *